United States Patent
Moloney

(10) Patent No.: US 11,154,578 B2
(45) Date of Patent: Oct. 26, 2021

(54) COMPOSITIONS AND METHODS OF USE

(71) Applicant: Melcare Medical Pty Ltd, Queensland (AU)

(72) Inventor: Anthony Peter Moloney, Queensland (AU)

(73) Assignee: MELGARE MEDICAL PTY LTD, Mount Cotton (AU)

( * ) Notice: Subject to any disclaimer, the term of this patent is extended or adjusted under 35 U.S.C. 154(b) by 858 days.

(21) Appl. No.: 15/327,970

(22) PCT Filed: Jul. 20, 2015

(86) PCT No.: PCT/AU2015/050405
§ 371 (c)(1),
(2) Date: Jan. 20, 2017

(87) PCT Pub. No.: WO2016/011498
PCT Pub. Date: Jan. 28, 2016

(65) Prior Publication Data
US 2017/0209500 A1    Jul. 27, 2017

(30) Foreign Application Priority Data
Jul. 22, 2014 (AU) .............................. 2014902829

(51) Int. Cl.
| | |
|---|---|
| *A61K 35/644* | (2015.01) |
| *A61K 9/00* | (2006.01) |
| *A61K 47/12* | (2006.01) |
| *A61K 9/08* | (2006.01) |
| *A61K 36/61* | (2006.01) |
| *A61K 35/63* | (2015.01) |
| *A61K 47/02* | (2006.01) |
| *A61L 15/40* | (2006.01) |

(52) U.S. Cl.
CPC .......... *A61K 35/644* (2013.01); *A61K 9/0043* (2013.01); *A61K 9/0048* (2013.01); *A61K 9/08* (2013.01); *A61K 35/63* (2015.01); *A61K 36/61* (2013.01); *A61K 47/02* (2013.01); *A61K 47/12* (2013.01); *A61L 15/40* (2013.01); *A61L 2300/30* (2013.01)

(58) Field of Classification Search
CPC ...... A61K 35/644; A61K 35/63; A61K 36/61; A61K 47/02; A61K 47/12; A61K 9/0043; A61K 9/0048; A61K 9/08; A61L 15/40; A61L 2300/30; A61P 11/02; A61P 11/04; A61P 17/02; A61P 27/02; A61P 27/16
USPC .................................................. 424/537, 539
See application file for complete search history.

(56) References Cited

FOREIGN PATENT DOCUMENTS

WO   WO 2007/137369 A1    12/2007
WO   WO-2007137369 A1 *  12/2007  ........... A61K 35/644

OTHER PUBLICATIONS

Bindu Nair "Final Report on the Safety Assessment of Benzyl Alcohol, Benzoic Acid, and sodium Benzoate" (Year: 2001).*
Albeitz et al., Effect of Antibacterial Honey on the Ocular Flora in Tear Deficiency and Meibomian Gland Disease, Cornea vol. 25, pp. 1012-1019, 2006.
Bakier, S., Influence of temperature and water content on the rheological properties of polish honeys, Polish Journal of Food and Nutrition Sciences, vol. 57, No. 2(A), pp. 17-23, 2007.
Loftsson, et al., Effect of Cyclodextrins on Topical Drug Delivery to the Eye, Drug Development and Industrial Pharmacy, vol. 23, No. 5, pp. 473-481, 1997.
Tan, et al., Effect of a formulated eye drop with *Leptospermum* spp honey on tear film properties, Br. J. Ophthalmol., 0:1-5. doi:10.1136/bjophthalmol-2019-315160, 2020.

* cited by examiner

*Primary Examiner* — Aaron J Kosar
(74) *Attorney, Agent, or Firm* — Knobbe, Martens, Olson & Bear LLP

(57) ABSTRACT

The present invention provides a composition comprising honey, a preservative and an aqueous carrier, wherein the honey is present in an amount in the range of from 2 to 50% w/w. Uses of the compositions of the invention for the management, treatment or prevention of a respiratory, ophthalmic, ear or vaginal condition in a subject, and for wound management are also described.

19 Claims, No Drawings

COMPOSITIONS AND METHODS OF USE

PRIORITY AND CROSS REFERENCE TO RELATED APPLICATIONS

This application is the U.S. National Stage Application under 35 U.S.C. § 371 of International Application No. PCT/AU2015/050405, filed Jul. 20, 2015, designating the U.S. and published in English as WO 2016/011498 A1 on Jan. 28, 2016, which claims the benefit of Australian Patent Application No. 2014902829, filed Jul. 22, 2014. Any and all applications for which a foreign or a domestic priority is claimed is/are identified in the Application Data Sheet filed herewith and is/are hereby incorporated by reference in their entirety under 37 C.F.R. § 1.57.

FIELD OF THE INVENTION

This invention relates to compositions comprising honey in an amount in the range of from 2 to 50% w/w, a preservative and an aqueous carrier. The composition of the invention may be used for the management, treatment or prevention of a respiratory, ophthalmic, ear or vaginal condition in a subject and for wound management.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The beneficial healing properties of honey have been known for thousands of years in traditional medicine. More recently a resurgence in the therapeutic interest in honey in mainstream medicine has occurred due to the appearance of experimental evidence demonstrating the beneficial effects of raw honey in wound care. This is most likely due to the inherent antimicrobial properties, particularly in certain types of honey.

The antimicrobial activity of honey has been related to several properties, including a high sugar content and low water activity, an acid pH (3.8 to 4.6), the presence of glucose oxidase (which catalyses the oxidation of glucose to hydrogen peroxide) and other less understood plant derived factors.

While all types of honey have some therapeutic properties, honey sourced from the Myrtacaea family, in particular *Leptospermum* species, is known to have a higher non-peroxide antimicrobial activity than other types of honey that is more stable to moderate heat, light and gamma radiation. These types of honey are substantially sourced from the *Leptospermum* species endemic to Australia and New Zealand.

While natural honey is effective in enhancing healing of wounds, it is difficult to use due to its stickiness and viscosity. However, several studies have recently emerged, which show that diluted *Leptospermum* species honey has an antibacterial effect against bacteria such as *Staphylococcus aureus, Pseudomonas aeruginosa, Acinetobacter baumanii, Enterobacter cloacae, Enterococcus faecalis, Escherichia coli, Klebsiella pneumoniae*, and Vancomycin Resistant *Enterococcus* (Alandejani T., et al., *Otolaryngol Head Neck Surg.*, 2009; 141(1)114-8; Jervis-Brady J., et al., *Laryngoscope*, 2011; 121(5):1104-7; George N. M. and Cutting K. F., *Wounds*, 2007; 19(9):231-6). These studies demonstrated that the *Leptospermum* species honey retained antibacterial activity when diluted to 33% w/v, but activity was lost at 16.5% w/v (Jervis-Brady J., et al., *Laryngoscope*, 2011; 121(5): 1104-7). Jervis Brady et al. (2011) describes the importance of methylglyoxal, one of the components of *Leptospermum* species honey, in the antibacterial activity of honey, showing that when methylglyoxal was added to non-*Leptospermum* species honey, some antibacterial activity was observed. Furthermore, compositions having 16.5% *Leptospermum* species honey which were not antibacterial were found to have antibacterial activity when supplemented with methylglyoxal (Jervis-Brady J., et al., *Laryngoscope*, 2011; 121(5): 1104-7). However, methylglyoxal was noted as not being solely responsible for the antibacterial effect of *Leptospermum* species honey. Other compositions comprising diluted honey are also known (WO/2007/137369 and Albeitz J. and Lenton L., *Optometry Pharma*, 2013; 28-30).

Although honey has inherent antimicrobial, antioxidant and other useful properties, many honey compositions do not meet the regulatory standards for product stability in multiple dose units, particularly when diluted. Such forms are preferred for daily and regular users of honey compositions to ensure convenient and cost effective therapies.

Additionally, lower concentrations of honey are desired for clinical use for easier application, and improve tolerability and affordability, while maintaining therapeutic activity. The viscous nature of undiluted and some diluted honey can make application difficult and the application to mucous membranes such as the eyes and nose can be messy and produce an initial stinging sensation and/or discomfort, thereby reducing patient compliance. Application is further complicated by the tendency of compositions containing high concentrations of honey to crystallise. A composition that avoids these problems, whilst meeting regulatory standards and retaining honey's clinical properties such as antimicrobial activity, low pH and inflammatory regulatory properties is desired for such applications.

SUMMARY OF THE INVENTION

The present invention is predicated in part on the discovery that compositions comprising honey in an amount in the range of from 2 to 50% w/w and a preservative in an aqueous carrier have comparable antimicrobial activity and clinical efficacy in vivo to the corresponding undiluted honey compositions, are easy to administer and in some cases reduce or eliminate stinging upon application.

In one aspect of the present invention, there is provided a composition comprising honey, a preservative and an aqueous carrier, wherein the honey is present in an amount in the range of from 2 to 50% w/w, wherein when the composition has ≥25% w/w honey, the composition is not in the form of a semi-solid cream.

In another aspect of the present invention, there is provided a method of treatment or prevention of a respiratory, ophthalmic, ear or vaginal condition in a subject, comprising administering to the subject a composition of the invention.

In a further aspect of the present invention, there is provided a use of a composition of the invention in the manufacture of a medicament for the treatment or prevention of a respiratory, ophthalmic, ear or vaginal condition in a subject.

In yet another aspect of the present invention, there is provided a method of hydrating a dressing, comprising contacting the dressing with a composition of the invention.

In a further aspect of the present invention, there is provided a method of hydrating or cleaning a wound, comprising contacting the wound with a composition of the invention.

In yet another aspect of the present invention, there is provided a method of incorporating a compound of the invention in a dressing by compounding it with the components of the dressing or by contacting the dressing with a composition of the invention.

In a further aspect of the present invention, there is provided a method of treating traumatised, damaged or vulnerable skin, comprising contacting the skin with a composition of the invention.

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The term "about" is used herein to refer to conditions (e.g., amounts, concentrations, time, etc.) that vary by as much as 30%, especially by as much as 20%, and more especially by as much as 10%, 9%, 8%, 7%, 6%, 5%, 4%, 3%, 2% or 1% to a specified condition.

The phrase "aqueous carrier" is used herein to refer to a liquid, aqueous diluent, wherein the aqueous carrier can be selected from the group including, but not limited to, water, saline, aqueous buffer and aqueous solutions comprising water soluble or water miscible additives such as glucose or glycerol. The aqueous carrier may also be in the form of an oil-in-water emulsion.

As used herein, the term "blepharitis" refers to an eye condition, characterised by chronic inflammation of the eyelid. Blepharitis may typically develop as a result of a bacterial infection of the eyelids, typically with a *Staphylococcus* species; mite infestation, a skin condition, such as seborrhoeic dermatitis or skin rosacea; meibomian gland dysfunction or any combinations thereof.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "condition" refers to an abnormality in the physical state of the body as a whole or one of its parts.

The phrase "dry eye syndrome" is used herein to refer to an ocular disorder of the normal tear film, resulting from decreased tear production, excessive tear evaporation or an abnormality in the production of mucus or lipids normally found in the tear layer. Dry eye syndrome may occur as a result of age; hormonal changes; autoimmune diseases, such as primary Sjögren's syndrome, rheumatoid arthritis, Stevens-Johnson syndrome, cicatricial pemphigoid or lupus erythematosus; medication use, such as antihistamines, antidepressants, beta-blockers, oral isotretinoin and oral contraceptives; lifestyle factors resulting in decreased blinking, such as tasks which require close visual attention; certain conditions resulting in an impaired ability to blink such as stroke or Bell's palsy; chemical burns to the eye; meibomian gland dysfunction; meibomian gland disease; rosacea; an infection, such as blepharitis; or trauma, such as surgery.

The term "infection" is used herein to refer to the invasion of a pathogen in any tissue or organ in a human or animal, wherein the pathogen may be selected from a bacteria; virus; fungi, such as yeast; protozoan species; and arthropod, such as a mite.

The phrase "*Leptospermum* species" refers to a genus of plants in the Myrtle family (Myrtaceae). This family includes, but is not limited to, the species *Leptospermum scoparium, Leptospermum polygalifolium, Leptospermum semibaccatum, Leptospermum trinervium, Leptospermum whitei, Leptospermum speciosum, Leptospermum petersonii* and *Leptospermum liversidgei.*

As used herein, the phrase "pharmaceutically acceptable salt" refers to a salt which is toxicologically safe for human and animal administration. The pharmaceutically acceptable salt may be selected from the group including, but not limited to, alkali metal such as sodium and potassium, alkali earth metal such as calcium and magnesium, ammonium, aluminium, iron, amine, glucosamine, chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, pamoate, pectinate and s-methyl methionine salts, piperazine and the like.

As used herein, the phrase "respiratory condition" refers to any disease, condition or disorder of the respiratory tract, wherein the respiratory tract includes the nose, nasal passages, sinuses, throat, pharynx, voice box, larynx, trachea, bronchi, bronchioles and lungs.

As used herein, the phrase "semi-solid cream" refers to a viscous, semi-solid preparation for topical application. "Semi-solid cream" includes water soluble cream compositions and ointments. As used herein, a semisolid is not pourable; it does not flow nor conform to its container at room temperature. It does not flow at low shear stress and generally exhibits plastic flow behaviour. A semi-solid dosage form usually contains water and volatiles and/or hydrocarbons, waxes, or polyols as the vehicle.

As used herein, the term "subject" refers to any mammalian or avian subject, for whom therapy or prophylaxis is desired. Suitable animals that fall within the scope of the invention include, but are not limited to, primates, avians, livestock animals (such as sheep, cows, horses, deer, donkeys, pigs), laboratory test animals (such as rabbits, mice, rats, guinea pigs, hamsters), companion animals (such as cats and dogs) and captive wild animals (such as those found in zoos). In particular, the subject is a human. However, it will be understood that the aforementioned terms do not imply that symptoms are present.

As used herein, the phrase "substantially sourced from *Leptospermum* species" refers to honey that is produced from nectar, at least 50%, especially at least 75%, and more especially at least 85%, 95% or 98% of which is sourced from one or more *Leptospermum* species.

2. Compositions of the Invention

In one aspect of the present invention, there is provided a composition comprising honey, a preservative and an aqueous carrier, wherein the honey is present in an amount in the range of from 2 to 50% w/w, wherein when the composition has ≥25% w/w honey, the composition is not in the form of a semi-solid cream.

The amount of honey in the composition may depend on the site of application and/or the condition being treated. In some embodiments, the honey in the composition is in an amount in the range of from 2 to 47% w/w, 2 to 45% w/w, 2 to 30% w/w, 2 to less than 25% w/w, 2 to less than 20% w/w, 5 to 19% w/w or 5 to 18% w/w, especially 7 to 18% w/w, more especially 10 to 18% w/w, even more especially 14 to 17% w/w or 15 to 17% w/w, most especially about 16.5% w/w. The inventors have surprisingly found that diluted honey has comparable clinical outcomes in vivo to that of the corresponding undiluted honey, is easy to administer and reduces stinging upon application.

The aqueous carrier may be any one of water, saline, aqueous buffer and an aqueous solution comprising water and a miscible solvent such as glycerol. In some embodiments, the aqueous carrier is water. In other embodiments, the aqueous carrier is saline. When saline is used, it is preferably isotonic for the point of administration, such as the eye. For example, in some embodiments the saline comprises 0.15 to 8% w/v sodium chloride, especially 0.18% to 7% w/v, 0.22% to 5% w/v, 0.45% to 3% w/v sodium chloride, more especially 0.5 to 2% w/v sodium chloride, more especially 0.65% to 1.5% w/v sodium chloride, most especially about 0.9% w/v sodium chloride.

In some embodiments where the aqueous carrier is not isotonic, for example water, the aqueous carrier may contain one or more tonicity agents. Suitable tonicity agents include, but are not limited to, any one of boric acid, sodium acid phosphate buffer, sodium chloride, glucose, potassium chloride, calcium chloride, magnesium chloride, polypropylene glycol, glycerol or salts or combinations thereof. The tonicity agent may be present in the composition in an amount that provides isotonicity with the point of administration such as the eye, for example in the range of from 0.02 to 15% w/w.

In other embodiments, the composition may be hyperisotonic, either by the amount of honey in the composition or the addition of further tonicity agent. A hyperisotonic composition may assist in reducing swelling in conditions where swelling is present.

In some embodiments the aqueous carrier is a buffer, wherein the buffer maintains a pH in the range of from 3 to 6, especially 3.5 to 6 or 3.8 to 5.6, more especially 3.8 to 4.6, most especially 3.8 to 4.2. Suitable buffering agents include, but are not limited to, acetic acid, citric acid, sodium metabisulphite, sodium bicarbonate, sodium hydroxide, boric acid, borax, alkali metal phosphates, phosphate and citrate buffers or combinations thereof. The buffering agent may be present in the composition in an amount suitable to maintain the desired pH.

In some embodiments, the pH of the composition is in the range of from 3.8 to 5.6, especially in the range of 3.8 to 4.6, more especially in the range of from 3.8 to 4.2. Without wishing to be bound by theory, it is thought that the pH of the honey, which is naturally buffered, triggers an initial inflammatory response in the subject.

In some embodiments, the preservative may include, but is not limited to, benzoic acid, flavonoids, phenolic acids, abscisic acid, sorbic acid, sodium perborate, stabilised oxychloro complex, polyquaternium-1, phenylmercuric acid, benzalkonium chloride, chlorbutanol, phenylmercuric acetate, phenylmercuric nitrate, chlorhexidine acetate, benzododecinium bromide, cetrimonium chloride, thiomersal, methyl parahydroxybenzoate, propyl parahydroxybenzoate, polyquaternium ammonium chloride, polyaminopropyl biguanide, hydrogen peroxide, ascorbic acid or pharmaceutically acceptable salts or combinations thereof. In particular embodiments, the preservative includes, but is not limited to, any one of benzoic acid, flavonoids, phenolic acids, abscisic acid, sorbic acid and pharmaceutically acceptable salts and combinations thereof; more especially the preservative comprises benzoic acid wherein the benzoic acid is in the form of a salt, especially sodium benzoate. In some embodiments, the preservative is a combination of sorbic acid or a salt thereof and benzoic acid or a salt thereof. Suitable flavonoids may include, but are not limited to, any one of flavonols, flavones, flavanones, isoflavones, anthocyanidins and combinations thereof, especially, myricetin, tricetin, quercitin, luteolin, kaempferol, kaempferol 8-methyl ether, pinocembrin and chrysin. Suitable phenolic acids may include, but are not limited to, gallic acid, ellagic acid, chlorogenic acid, caffeic acid, p-coumaric acid, ferulic acid, syringic acid or combinations thereof. The preservative may be present in the composition in an amount that provides adequate preservative activity. For example, the preservative may be present in an amount in the range of from 0.001 to 0.7%, 0.002 to 0.6%, 0.003 to 0.5%, 0.004 to 0.5%, 0.005 to 0.5%, 0.01 to 0.4%, 0.05 to 0.4% w/w; especially 0.05 to 0.3% w/w; most especially about 0.05 to 0.25% w/w.

Preservative activity is particularly desirable for compositions of the invention in multiple dose units. Honey contains several compounds that have antioxidant or antimicrobial activity and, therefore, act as natural preservatives. However, these compounds are not present in sufficient amounts, particularly in diluted honey, to provide adequate preservative activity or to meet the required pharmaceutical standards. Advantageously, in the compositions of the invention, lower amounts of preservative may be added due to the inherent stability of honey. In particular embodiments, the composition of the invention includes the addition of one or more of the above preservative compounds to supplement natural preservatives found in the honey but in sub-effective amounts after dilution of the honey. For example, in particular embodiments, the preservative may include, but is not limited to, one or more of abscisic acid, sodium benzoate, flavonoids, benzoic acid, phenolic acids and combinations thereof. This may avoid the tendency of the subjects to develop acute sensitivity to preservatives, particularly those that are commonly used in ophthalmic compositions. In some embodiments, the preservative acts together with natural honey preservatives.

In some embodiments, the honey used is natural raw honey sourced from any plant species. Such honey compositions may be useful in treating or preventing conditions in which the soothing or healing effects of honey are required, for example, in treating dry eye syndrome or when used in conjunction with an antibiotic therapy.

In some embodiments, particularly where some antimicrobial activity may be advantageous, the honey in the composition is substantially sourced from *Leptospermum* species. In some embodiments, the *Leptospermum* species is any one of *Leptospermum scoparium, Leptospermum polygalifolium, Leptospermum semibaccatum, Leptospermum trinervium, Leptospermum whitei, Leptospermum speciosum, Leptospermum liversidgei* and combinations thereof. *Leptospermum* species honey is bacteriostatic at low concentrations.

In some embodiments, the composition further comprises a rheology modifier that alters the surface tension and flow of the composition. Suitable rheology modifiers include, but are not limited to, hydrocolloids, gum arabic, xanthan gum, guar gum, locust bean gum, carboxymethylcellulose, alginate, starch (from rice, corn, potato or wheat), carrageenan, konjac, aloe vera gel, agarose, pectin, tragacanth, curdlan gum, gellan gum, scleroglucan, hyaluronic acid, chitosan-polyvinyl alcohol or derivatives thereof, polyvinyl alcohol, polyethylene glycol, polyvinyl pyrrolidone, Carbopol or derivatives thereof, dextran, methylcellulose, hydroxypropylmethyl cellulose, hydroxyethylcellulose, hydroxypropylcellulose, hydroxypropyl guar or combinations thereof. In particular embodiments, the rheology modifier is any one of gum arabic, xanthan gum, guar gum, locust bean gum, carboxymethylcellulose, alginate, starch (from rice, corn, potato or wheat) and combinations thereof, especially gum arabic.

In some embodiments, the composition of the invention may further comprise one or more polysaccharides that may have other therapeutic properties useful for the composition but may not be classed as rheology modifiers. For example, in some embodiments, the polysaccharides include, but are not limited to, any one or more of chitosans, chitins, dermatans, hyaluronates, heparans, dermatans, chondroitins, heparins and combinations thereof.

The composition may also further comprise one or more surfactants or wetting agents, wherein the surfactant or wetting agent includes, but is not limited to, benzalkonium chloride, Cetomacrogol 1000, polysorbate, dioctyl sodium sulphosuccinate, fatty alcohol ethoxylates, alkylphenol polyethylene glycols, alkyl mercaptan polyethylene glycols, fatty amine ethoxylates, fatty acid ethoxylates, polypropylene glycol ethoxylates, fatty acid alkylolamides, alkyl polyglycosides, N-alkylpolyhydroxy fatty acid amide, N-alkoxypolyhydroxy fatty acid amide, sucrose esters, sorbitol esters, esters of sorbitol polyglycol ethers or combinations thereof. Surfactants may be useful in emulsifying the aqueous carrier with an oil when an oil is included in the composition. Surfactants and wetting agents may also be useful to improve cleaning or mobility of fatty acids, for example, from the meibomian glands. In some embodiments, the surfactant or wetting agent may be present in an amount in the range of from 0.5 to 7% w/w, especially 1 to 5% w/w.

The composition may also further comprise one or more chelating agents. Suitable chelating agents include, but are not limited to, amino carboxylic acids and salts thereof such as ethylenediamine tetraacetic acid (EDTA), nitrilotriacetic acid, nitrilotripropionic acid, diethylenetriamine pentacetic acid, 2-hydroxyethyl-ethylenediamine-triacetic acid, 1,6-diamino-hexamethylene-tetraacetic acid, 1,2-diamino-cyclohexane tetraacetic acid, O,O'-bis(2-aminoethyl)-ethyleneglycol-tetraacetic acid, 1,3-diaminopropane-tetraacetic acid, N,N-bis(2-hydroxybenzyl)ethylenediamine-N,N-diacetic acid, ethylenediamine-N,N'-diacetic acid, ethylenediamine-N,N'-dipropionic acid, triethylenetetraamine hexaacetic acid, 7,19,30-trioxa-1,4,10,13,16,22,27,33-octaazabicyclo[11,11,11]pentatriacontane (O-bis-tren), ethylenediamine-N,N'-bis(methylenephosphonic acid), iminodiacetic acid, N,N-bis(2-hydroxyethyl)glycine (DHEG), 1,3-diamino-2-hydroxypropane-tetraacetic acid, 1,2-diaminopropane-tetraacetic acid, ethylenediamine-tetrakis (methylenephosphonic acid), N-(2-hydroxyethyl) iminodiacetic acid or triethylenetetraamine-hexaacetic acid or pharmaceutically acceptable salts thereof; especially pharmaceutically acceptable salts or mixed salts of EDTA, such as disodium, trisodium, tetrasodium, dipotassium, tripotassium, lithium, dilithium, ammonium, diammonium, calcium or calcium-disodium; more especially disodium or tetrasodium salts of EDTA; most especially disodium EDTA.

The composition may also further comprise one or more alcohols. Suitable alcohols include, but are not limited to, isopropanol, benzyl alcohol, cetearyl alcohol or ethanol. The alcohol may be present in the composition in an amount in the range of from 0.2 to 12% w/w.

The composition may also further comprise one or more oils. Suitable oils include, but are not limited to, almond oil including sweet almond oil, castor oil, mineral oil, citrus oil, clove oil, tea tree oil, olive oil, peanut oil, coconut oil, soybean oil, lavender oil, garlic oil or seed oils such as canola oil, cottonseed oil, linseed oil, grapeseed oil, safflower oil, sesame oil or sunflower oil; especially almond oil; more especially sweet almond oil. Such oils may be included in the composition in the form of an oil-in-water emulsion, optionally with a surfactant, with the aqueous carrier. The oil may be present in an amount in the range of from 0.2 to 20% w/w.

In some embodiments, the composition further comprises one or more lubricants. Suitable lubricants include, but are not limited to, glucose, glycerol, polyethylene glycol or propylene glycol. The lubricant may be present in an amount in the range of from 0.2 to 20% w/w.

The composition may comprise or may be administered separately, simultaneously or sequentially with one or more pharmaceutically active agents. The pharmaceutically active agent may include, but is not limited to, a steroid such as betnesol, prednisolone, beclometasone, betamethasone, budesonide, fluticasone, flunisolide, mometasone, triamcinolone, dexamethasone, fluocinolone or hydrocortisone; an antibiotic agent such as gentamycin, neomycin, quinolenes, metronidazole, clindamycin, dibrompropamidine, sulfacetamide, chloramphenicol, ciprofloxacin, tobramycin, polymyxin, ofloxacin, framycetin, fusidic acid, tetracyclines or gramicidin; an antifungal agent such as clotrimazole, polysorbate, gentian violet, nystatin or miconazole; an antimicrobial agent such as sorbic acid, chlorhexidine, polyhexamethylene biguanide or chlorobutanol; an antibacterial agent, such as methylglyoxal or the methylglyoxal precursor, dihydroxyacetone; an immunosuppressive agent such as cyclosporine; an anti-allergy agent such as an antihistamine or a mast cell stabiliser; a vasoconstrictor such as naphazoline, phenylephrine, oxymetazoline or tetrahydrozoline; an antiviral such as aciclovir; a decongestant such as xylometazoline; an anti-hypertensive agent such as p-amino clonidine; an anti-glaucoma agent such as a prostaglandin analogue (latanoprost, bimatoprost, travoprost), a beta blocker (timolol, betaxolol), an alpha agonist (brimonidine, apraclonidine) or a carbonic anhydrase inhibitor (dorzolamide, brinzolamide); a neuro-protective agent; an anaesthetic agent such as benzocaine or pramocaine; a muco-secretagogue agent; an angiostatic agent; and an anti-inflammatory agent such as a non-steroidal anti-inflammatory drug, including naproxen, diclofenac, phenazone, suprofen or ketorolac; pilocarpine; a prostaglandin; a dopaminergic antagonist; a protein; a growth factor; a hyaluronate; hyaluronic acid; ipratropium; albuterol; or pharmaceutically acceptable salts or combinations thereof. In particular embodiments, the pharmaceutically active agent is selected from sorbic acid, chloramphenicol, methylglyoxal and dihydroxyacetone; especially methylglyoxal. In some embodiments, the composition of the invention does not contain added methylglyoxal.

The composition may further comprise other natural remedies or plant extracts. For example, the composition may further comprise herbs or fungi or extracts thereof, such as those used in traditional herbology, including Chinese herbology, Islamic herbology and Indian herbology; or plant and/or flower extracts, such as lavender, jasmine, violet, rose, marigold, chamomile, frangipani, cactus flower, aloe vera, jojoba, rosehip, pomegranate, green tea, lemongrass, mint, linden flower, *Glycyrrhiza uralensis, Panax ginseng, Arnica montana* or honeysuckle flower extract, or combinations thereof.

In some embodiments, the composition of the invention may further comprise one or more antioxidants. Suitable antioxidants include, but are not limited to, vitamin E or tocopherol, vitamin C or ascorbic acid, ubiquinone, idebenone, lycopene, resveratrol or niacinamide. The antioxidant may be present in an amount in the range of from 0.1 to 4% w/w.

In some embodiments, the composition of the invention is formulated for example as an emulsion, cream, lotion, gel, jelly, paste, ointment, solution, salve, solution or suspension, especially as a emulsion, cream, lotion, gel, paste, ointment, solution, or suspension, as described in, for example, the United States Food and Drug Administration Monograph No. C-DRG-00201 entitled CDER Data Standards Manual Definitions for Topical Dosage Forms. In some embodiments, the composition of the invention is a solution.

In some embodiments, the composition of the invention is in the form of a nasal lavage, nasal spray, eye drop, eye spray, eye wash, ear wash, ear drop, throat spray, douche, wound dressing hydrator, lung aspirant, lotion or cream, especially a nasal lavage, nasal spray, eye drop, eye spray, eye wash, ear wash, ear drop, throat spray, douche, wound dressing hydrator or lung aspirant. In a further embodiment the lung aspirant may be suitable for use in a subject with cystic fibrosis. In some embodiments, the composition of the invention is in a multiple dose unit.

The compositions of the invention may be readily prepared by mixing the ingredients. In some cases, the preservative is dissolved in the aqueous carrier and warmed to 40° C. to 55° C. The honey is then mixed in and the temperature maintained between 40° C. and 55° C. while mixing for 20 minutes to 1 hour. The mixture is allowed to cool and the pH adjusted to 3.8 to 4.2 if necessary. The composition may then be sterilised by filtration and/or gamma irradiation.

Prior to use, the composition may be subjected to gamma irradiation, filtering or combinations thereof to remove pollen and remove or kill clostridial spores or other contaminants that may be naturally present in the honey. In some embodiments, the filter may remove particles of greater than 25 especially greater than 10 most especially greater than 5 μm.

3. Methods of the Invention

In another aspect of the present invention, there is provided a method of treatment or prevention of a respiratory, ophthalmic, ear or vaginal condition in a subject, comprising administering to the subject a composition of the invention.

In some embodiments, the respiratory condition includes, but is not limited to, any one or more of infections associated with cystic fibrosis, tuberculosis and AIDS; lung and bronchopulmonary infections, including those caused by *Pseudomonas aeruginosa, Pneumocystis carinii, Staphylococcus aureus, Haemophilus influenzae, Mycobacterium tuberculosis, Mycobacterium bovis, Mycobacterium africanum, Mycobacterium canetti* and *Mycobacterium microti*; sinusitis or rhinosinusitis, including acute rhinosinusitis, recurrent acute rhinosinusitis, subacute rhinosinusitis, chronic rhinosinusitis and acute exacerbation of chronic rhinosinusitis; rhinitis, including infective, allergic and non-allergic (vasomotor) rhinitis; pharyngitis; tonsillitis; laryngitis; and bacterial infections of the nasal cavity, such as those due to *Klebsiella ozenae* and *S. aureus*. Suitably, the compositions of the invention may be administered as a nasal lavage, nasal spray, throat spray or lung aspirant.

In some embodiments, the ophthalmic condition includes, but is not limited to, any one or more of blepharitis, dry eye syndrome, conjunctivitis, keratitis, kerato-conjunctivitis, herpes simplex virus infection, Fuch's dystrophy, Sjögren's syndrome, non-Sjögren's syndrome and acanthmoeba. In some embodiments, the ophthalmic condition includes, but is not limited to, corneal oedema. In some embodiments, the ophthalmic condition includes, but is not limited to, allergic conjunctivitis or rhinoconjunctivitis. Suitably, the compositions of the invention may be administered as an eye drop or eye wash.

In some embodiments, the ear condition includes, but is not limited to, otitis, for example otitis externa, otitis media or otitis interna. Suitably, the compositions of the invention may be administered in the form of an ear drop or ear lavage.

In some embodiments, the vaginal condition includes, but is not limited to, any one or more of vaginitis, such as bacterial vaginosis, especially infections caused by *Streptococcus* species and *Gardnerella vaginalis*, vaginal candidiasis, especially infections caused by *Candida* species, more especially infections caused by *Candida albicans*, and trichomoniasis, especially infections caused by *Trichomonas vaginalis*; infections caused by *Mycoplasma* species; herpes simplex virus infections; and other sexually transmitted infections or diseases, such as *chlamydia* and gonorrhoea. Suitably, the compositions of the invention may be administered as a douche. The use of a douche comprising honey creates a low pH environment in the vagina that favours non-pathogenic commensal or mutualistic microflora.

Without wishing to be bound by theory, it is thought that the honey in the composition may stimulate an immune response to inflammation, thereby enhancing the subject's immune system and assisting in the therapy of the condition.

In some embodiments, the condition is associated with inflammation or infection. In some embodiments the respiratory, ophthalmic, ear or vaginal condition is associated with inflammation. In some embodiments the respiratory, ophthalmic, ear or vaginal condition is associated with infection. The infection may be caused by, but is not limited to, bacteria, fungi such as yeast, virus, protozoan species or arthropod such as a mite. In some embodiments, the condition is any one of ophthalmic infection, vaginal infection, nasal infection, ear infection, lung infection, sinus infection, throat infection and sore throat.

In some embodiments, the respiratory, ophthalmic, ear or vaginal condition may include, but is not limited to, trauma, such as surgery.

In some embodiments, the condition is blepharitis, dry eye syndrome, rhinitis or sinusitis. In some embodiments, the condition is corneal oedema. In some embodiments, the blepharitis has developed as a result of, but is not limited to, any one or more of a bacterial infection of the eyelids, typically with a *Staphylococcus* species; mite infestation; a skin condition, such as seborrhoeic dermatitis or skin rosacea; meibomian gland dysfunction and any combinations thereof. In some embodiments, the dry eye syndrome has occurred as a result of, but is not limited to, any one or more of age; hormonal changes; autoimmune diseases, such as primary Sjögren's syndrome, rheumatoid arthritis, Stevens- Johnson syndrome, cicatricial pemphigoid or lupus erythematosus; medication use, such as use of antihistamines, antidepressants, beta-blockers, oral isotretinoin and oral contraceptives; lifestyle factors resulting in decreased blinking, such as tasks which require close visual attention; certain conditions resulting in an impaired ability to blink such as stroke or Bell's palsy; chemical burns to the eye; meibomian gland dysfunction; meibomian gland disease; rosacea; an infection, such as blepharitis; or trauma, such as surgery. In some embodiments, the corneal oedema has developed as a result of eye surgery such as cataract surgery or a corneal transplant, infection such as herpes simplex virus infection, glaucoma or Fuch's dystrophy. In certain embodiments, rhinitis includes, but is not limited to, infective, allergic and nonallergic (vasomotor) rhinitis. In particular embodiments, sinusitis or rhinosinusitis includes, but is not limited to, acute rhinosinusitis, recurrent acute rhinosinusitis, subacute rhinosinusitis, chronic rhinosinusitis or acute exacerbation of chronic rhinosinusitis.

In some embodiments, the method alleviates the symptoms of a respiratory, ophthalmic, ear or vaginal condition. For example, in some embodiments, the method of the invention alleviates the symptoms of dry eye syndrome, blepharitis, rhinitis or sinusitis without necessarily curing the condition. In some embodiments, the methods reduce inflammation that may be present in a subject having a respiratory, ophthalmic, ear or vaginal condition.

In a further aspect of the present invention, there is provided a use of a composition of the invention in the manufacture of a medicament for the treatment or prevention of a respiratory, ophthalmic, ear or vaginal condition in a subject.

In some embodiments of the present invention, there is provided a method of treatment or prevention of a condition associated with inflammation or infection of an epithelial lined surface, especially a mucosal epithelial lined surface. The epithelial lined surface may include, but is not limited to, the outside or inside cavities or lumen of bodies such as the skin, tissue lining the mouth, nose, sinus, oesophagus or lungs; tissue lining the rectum or anus; tissue lining the vagina or urethra; tissue lining the outer surface of the cornea; or tissue lining the ears. A mucosal epithelial lined surface includes, but is not limited to, the surface of the respiratory tract, including the sinus, mouth, nose and oesophagus; or the surface of the ears, eyes, genitals or anus.

In some embodiments, the compositions of the invention may be used in the manufacture of a medicament, to lubricate the eye or provide or supplement artificial tear compositions to prevent or treat ophthalmic conditions, such as, but not limited to, dry eye syndrome. In some embodiments, the compositions of the invention may be used in the manufacture of a medicament, to lubricate the eye or provide or supplement artificial tear compositions to prevent or treat ophthalmic conditions, such as, but not limited to, corneal oedema.

In some embodiments, the ophthalmic compositions may be applied to the eye as a wash, drop, irrigation, flush, rinse or lavage. In other embodiments, the compositions may be applied to the ear as a drop, wash, lavage, irrigation, flush, rinse or may be syringed. In yet other embodiments, the compositions may be applied to the vagina as a douche. In further embodiments, the composition may be applied to the respiratory tract by flushing, washing, lavage, irrigation, rinsing, drops, aspirant or spray.

Dosage or treatment regimes may be established for different indications in accordance with methodologies well known to a person skilled in the art. In some embodiments, treatment for ophthalmic conditions may include about 2 to 8 drops per eye daily. In some embodiments, treatment for the respiratory tract may include about 2 to 4 sprays daily. In some embodiments, treatment for the ear may include about 2 to 20 drops in the affected ear daily.

In some embodiments, the compositions of the invention may be used to treat or prevent more than one condition concurrently. For example, the compositions of the invention may be used to treat or prevent an ophthalmic condition and a respiratory condition concurrently, preferably dry eye syndrome and rhinosinusitis or sinusitis, such as by administering eye drops and nasal spray concurrently. In particular embodiments, the compositions of the invention are used to treat or prevent rhinoconjunctivitis or allergic conjunctivitis and/or rhinosinusitis.

In some embodiments, the compositions of the invention may be administered by more than one route of administration concurrently, for example, eye drops and nasal spray.

The ophthalmic compositions of the invention may be used with both hard and soft contact lenses. The ophthalmic compositions of the invention may be combined with artificial tear preparations.

In a yet further aspect of the present invention, there is provided a method of incorporating a composition of the invention into a dressing, comprising either compounding the composition with the components of the dressing, or contacting the dressing with a composition of the invention.

In yet another aspect of the present invention, there is provided a method of hydrating a dressing, comprising contacting the dressing with a composition of the invention.

In a yet further aspect of the present invention, there is provided a method of hydrating a wound or a wound dressing, comprising contacting the dressing with a composition of the invention.

Examples of dressings include wound dressings, sanitary dressings and breast pads. In some embodiments sanitary dressings include absorbent sanitary pads, napkins and tampons. Suitable sanitary dressings may include, but are not limited to, cotton, rayon, bleached wood pulp, sphagnum and polyacrylate gels. Suitable breast pads may include, but are not limited to bamboo, cotton and rayon. In some embodiments, the wound dressing is an absorbent dressing. In some embodiments the dressing is a wound dressing. Suitable wound dressings may include, but are not limited to, gauze including acetate gauze or Telfa dressings, sponge, pads, packing strips, tulle and foam dressings, gels or hydrocolloid sheets. In some embodiments, the wound dressing may be a primary or secondary dressing. In a particular embodiment the wound dressing is a hydrocolloid dressing.

In another aspect of the present invention, there is provided a method of hydrating or cleaning a wound, comprising contacting the wound with a composition of the invention. In particular embodiments, the compositions of the invention may be contacted with the wound by washing, rinsing, flushing, lavage or irrigation.

In some embodiments, the wound may be any one of, but is not limited to, a superficial, partial and full thickness wound. In some embodiments, the wound may be any one of, but is not limited to, surgical incisions, burns, cuts, scrapes, abrasions, venous stasis and ulcerations including pressure ulcers and diabetic skin ulcers. In particular embodiments, the hydrated wound dressing is used to soften necrotic tissue. In further embodiments, the hydrated wound dressing is used to remove necrotic tissue.

In some embodiments, when the composition of the invention has ≥25% w/w honey, the composition is not in the form of a semi-solid cream. In other embodiments, when the composition of the invention has <25% w/w honey, the composition may be in the form of a semi-solid cream. In some embodiments, the semi-solid cream may be topically applied to the skin, for example, for wound cleansing or hydrating.

EXAMPLES

Prior to incorporation into a preserved formulation, the honey is processed by blending to ensure homogeneity, preferably using a low shear mixer. The honey is then heated to dissolve any crystals that may have formed during storage. Preferably the honey is heated to temperatures of less than 75° C. The honey is filtered to remove undissolved crystals and any extraneous matter. Preferably the honey is filtered through a 5-10 μm filter using pressure filtration. Prior to filtration, the honey may be centrifuged to aid the removal of wax.

Example 1: Method of Producing Preserved Formulation

The water is heated to between 45 and 55° C. Sodium benzoate is then dissolved in the heated water. When the sodium benzoate is dissolved, honey and sodium chloride (if used) are added to the solution and the solution is stirred for 45 mins at a temperature of between 45 and 55° C. The solution is then cooled to between 40 and 45° C. and the pH adjusted to between 4.0 and 4.2 with citric acid if required. The resulting solution is then filtered through a 5 μm filter, before being subjected to gamma radiation.

Example 2: Stability of Preserved Honey Formulations

Samples of composition A (aqueous 8% w/w honey and 0.1% w/w benzoic acid, pH 4.04) and composition B (aqueous 25% w/w honey and 0.1% w/w benzoic acid, pH 4.04) were prepared according to the method of Example 1 and stored in opaque containers at 20 to 25° C.

Samples were challenged with *Pseudomonas aeruginosa, Staphylococcus aureus, Escherichia coli, Candida albicans, Aspergillus brasiliensis* and *Zygosaccharomyces rouxii* by adding inoculum to a sample and recovering microorganisms from the inoculated sample. The samples were challenged with a first inoculum of the test microorganism, followed by a second inoculum at day 14, a third inoculum at day 21, a fourth inoculum at week 6 and a fifth inoculum at week 9. The amount of microorganisms present in the test honey samples was determined at defined intervals throughout the study period. This study was performed in accordance with ISO 14730:2000(E) Ophthalmic optics—Contact lens care products—Antimicrobial preservative efficacy testing and guidance on determining discard date, Annex B—Discard date procedure I. The results are shown in Tables 1 and 2.

Samples of composition C (aqueous 35% w/w honey, 0.9% w/w NaCl, 0.2% w/w benzoic acid) were prepared according to the method of Example 1 and stored in opaque containers at 20 to 25° C.

Samples were challenged with *Pseudomonas aeruginosa, Staphylococcus aureus, Escherichia coli, Candida albicans, Aspergillus niger* and *Zygosaccharomyces rouxii* by adding inoculum to a sample and recovering microorganisms from the inoculated sample. The samples were challenged with a single inoculum of the test microorganism. The amount of microorganisms present in the test honey samples was determined at defined intervals throughout the study period. This study was performed in accordance with the guidelines of British Pharmacopoeia Appendix XVI C, 2012. The results are shown in Table 3.

As can be seen from Tables 1 and 2, both compositions A and B retained antimicrobial activity throughout the test period. Interestingly, composition A (8% honey) had comparable antimicrobial activity to composition B (25% honey) against all microorganisms tested.

Composition C (35% honey) also retained its antimicrobial activity throughout the study period.

TABLE 1

Antimicrobial activity of composition A.

| | Microorganism Counts (CFU/gram) | | | | | | | | | | | | |
|---|---|---|---|---|---|---|---|---|---|---|---|---|---|
| Test Organism | $1^{st}$ inoculum | 0 hours | Day 7 | Day 14 | $2^{nd}$ inoculum | Day 21 | $3^{rd}$ inoculum | Day 28 | 6 weeks | $4^{th}$ inoculum | 9 weeks | $5^{th}$ inoculum | 12 weeks |
| *S. aureus* | $2.4 \times 10^6$ | $2.0 \times 10^6$ | ≈10 | <10 | $1.5 \times 10^3$ | <10 | $4.9 \times 10^3$ | <10 | <10 | $9.9 \times 10^3$ | <10 | $7.1 \times 10^3$ | <10 |
| *P. aeruginosa* | $4.5 \times 10^5$ | $<1.0 \times 10^2$ | ≈13 | <10 | $2.5 \times 10^3$ | <10 | $2.9 \times 10^3$ | <10 | <10 | $4.5 \times 10^3$ | <10 | $1.5 \times 10^3$ | <10 |
| *E. coli* | $3.8 \times 10^6$ | $≈5.4 \times 10^6$ | $3.0 \times 10^2$ | ≈10 | $1.2 \times 10^3$ | ≈53 | $5.2 \times 10^3$ | <10 | <10 | $4.0 \times 10^3$ | <10 | $9.9 \times 10^3$ | <10 |
| *C. albicans* | $3.8 \times 10^5$ | $5.6 \times 10^5$ | $2.9 \times 10^4$ | <10 | $1.3 \times 10^3$ | $4.3 \times 10^3$ | $4.4 \times 10^3$ | <10 | <10 | $8.2 \times 10^3$ | <10 | $5.9 \times 10^3$ | <10 |
| *A. brasiliensis* | $1.5 \times 10^5$ | $1.6 \times 10^5$ | <10 | <10 | $2.5 \times 10^3$ | <10 | $1.9 \times 10^3$ | <10 | <10 | $3.9 \times 10^3$ | <10 | $6.0 \times 10^3$ | <10 |
| *Z. rouxii* | $3.9 \times 10^5$ | $3.5 \times 10^5$ | <100 | <10 | $1.0 \times 10^3$ | <10 | $7.4 \times 10^3$ | <10 | <10 | $8.6 \times 10^3$ | <10 | $1.1 \times 10^3$ | <10 |

TABLE 2

Antimicrobial activity of composition B.

| Test Organism | 1st inoculum | 0 hours | Day 7 | Day 14 | 2nd inoculum | Day 21 | 3rd inoculum | Day 28 | 6 weeks | 4th inoculum | 9 weeks | 5th inoculum | 12 weeks |
|---|---|---|---|---|---|---|---|---|---|---|---|---|---|
| S. aureus | $2.4 \times 10^6$ | $7.2 \times 10^5$ | ≈50 | <10 | $1.5 \times 10^3$ | <10 | $4.9 \times 10^3$ | <10 | <10 | $9.9 \times 10^3$ | <10 | $7.1 \times 10^3$ | <10 |
| P. aeruginosa | $4.5 \times 10^5$ | $<1.0 \times 10^2$ | ≈67 | $<3.0 \times 10^3$ | $2.5 \times 10^3$ | <10 | $2.9 \times 10^3$ | ≈23 | <10 | $4.5 \times 10^3$ | <10 | $1.5 \times 10^3$ | <10 |
| E. coli | $3.8 \times 10^6$ | $≈3.5 \times 10^6$ | ≈67 | ≈37 | $1.2 \times 10^3$ | <10 | $5.2 \times 10^3$ | ≈63 | <10 | $4.0 \times 10^3$ | <10 | $9.9 \times 10^3$ | <10 |
| C. albicans | $3.8 \times 10^5$ | $5.0 \times 10^5$ | $60 \times 10^2$ | <10 | $1.3 \times 10^3$ | $8.3 \times 10^2$ | $4.4 \times 10^3$ | <10 | <10 | $8.2 \times 10^3$ | <10 | $5.9 \times 10^3$ | <10 |
| A. brasiliensis | $1.5 \times 10^5$ | $2.2 \times 10^5$ | <10 | <10 | $2.5 \times 10^3$ | <10 | $1.9 \times 10^3$ | <10 | <10 | $3.9 \times 10^3$ | <10 | $6.0 \times 10^3$ | <10 |
| Z. rouxii | $3.9 \times 10^5$ | $3.8 \times 10^5$ | <100 | <10 | $1.0 \times 10^3$ | <10 | $7.4 \times 10^3$ | <10 | <10 | $8.6 \times 10^3$ | <10 | $1.1 \times 10^3$ | <10 |

TABLE 3

Antimicrobial activity of composition C.

| Test Organism | 1st inoculum | 0 hours | 6 hours | 24 hours | 48 hours | 7 days | 14 days | 28 days |
|---|---|---|---|---|---|---|---|---|
| S. aureus | $2.1 \times 10^6$ | $1.0 \times 10^5$ | <100 | <10 | <10 | <10 | — | <10 |
| P. aeruginosa | $1.2 \times 10^6$ | $<1.0 \times 10^3$ | <100 | <10 | <10 | <10 | — | <10 |
| E. coli | $1.8 \times 10^6$ | $<1.0 \times 10^3$ | <100 | <10 | <10 | <10 | — | <10 |
| C. albicans | $2.5 \times 10^5$ | $2.4 \times 10^5$ | — | — | — | — | <10 | <10 |
| A. niger | $4.1 \times 10^5$ | $1.8 \times 10^5$ | — | — | — | — | <10 | <10 |
| Z. rouxii | $2.4 \times 10^5$ | $<1.0 \times 10^2$ | — | — | — | — | <10 | <10 |

Example 3: Effect of a Honey Solution on Subjects with Dry Eye Syndrome Due to Meibomian Gland Disease A clinical trial was performed to evaluate the whether a honey solution is a safe and effective treatment in controlling the signs and symptoms of dry eye syndrome.

80 human subjects with dry eye syndrome as a result of meibomian gland disease were selected based on key inclusion and exclusion criteria. Inclusion criteria included: male or female patients over 18 years of age; provision of written informed consent to participate in the study; and chronic tear film and/or ocular surface dysfunction non-responsive to topical treatments. Exclusion criteria included: known allergy to pollen or honey bee hive products; known allergy to topical anaesthetic eye drops or vital stains used in data collection; multiple ocular and/or systemic allergies; non-compliance with honey treatment schedule or review visit schedule; no active intra-ocular inflammation; no systemic bacterial, viral or fungal disease; and/or no concurrent use of topical antibiotics or topical ocular steroids.

Prior to the commencement of the study a one month washout period occurred. During this period, subjects discontinued use of all topical medication, maintained lid hygiene twice daily and used non-preserved lubricant eye drop supplements (Systane Ultra) as required.

During the trial period, a honey/saline solution containing 16.5% w/w honey, 0.9% w/w NaCl and 0.2% w/w benzoic acid (prepared according to the method of Example 1) was applied topically to subjects. One drop of the honey solution was applied to the eye twice daily for a period of one month. The subjects also continued to maintain lid hygiene twice daily and used non-preserved lubricant eye drop supplements (Systane Ultra) as required.

Efficacy of the treatment was evaluated using a series of clinical techniques based on the best-practice methodology described in the Report of the National Eye Institute/Industry Workshop on Clinical Trials in Dry Eyes (Lemp M. A., *CLAO J*, 1995; 21:221-32) at the day of commencement of treatment and 1 month after commencement of treatment. These techniques included: visual acuity; signs and symptoms of dry eye syndrome, including Ocular Surface Disease Index (OSDI) which is a validated dry eye symptom survey, tear secretion or Schirmer test, tear film stability or tear break up time (TBUT) which is a non-invasive test using videokeratoscopy, and lissamine green and fluorescein staining which is graded by Oxford staining score; tear osmolarity; tear inflammation determined by Matrix metalloproteinase 9 (MMP 9) measurement; lid margin swabs for cultures/sensitivities; and safety which was evaluated by the adverse effects.

70 subjects completed the trial (Table 4). Administration of honey composition C significantly improved the signs and symptoms of dry eye syndrome.

10 subjects dropped out of the trial. 5 subjects noted significant improvement in symptoms after the washout period, 1 subject had blepharoplasty during the trial and 4 subjects could not tolerate the initial stinging sensation upon administration. The only adverse reaction reported was an initial stinging sensation upon administration of the honey solution in all patients lasting between 10 seconds and several minutes.

TABLE 4

Efficacy of honey composition C in subjects with dry eye syndrome.

| Assessments | Pre-honey Mean (SD) | After Honey Mean (SD) | Significance |
|---|---|---|---|
| OSDI | 42.27 (22.96) | 26.17 (19.92) | P < 0.0001 |
| Schirmer test | 9.76 (9.47) | 11.14 (9.48) | NS P = 0.065 |
| TBUT | 3.58 (1.98) | 4.59 (1.93) | P = 0.001 |
| Staining | 5.74 (4.13) | 2.51 (2.94) | P < 0.0001 |
| MMP 9 | 40% (28/70) | 10% (7/10) | |
| Osmolarity | 306.37 (9.92) | 303.07 (14.22) | P = 0.03 |
| Corneal Sensation | 5.44 (0.62) | 5.53 (1.00) | NS P = 0.487 |
| MG Expression Score | 1.0 (0.99) | 0.43 (1.16) | P = 0.0005 |
| MG Secretion Score | 14.9 (5.25) | 8.10 (6.16) | P < 0.0001 |
| Lid Margin Bacteria | 25.7% (18/70) | 2.86% (2/70) | |
| Lubricant Free Days | 0.80 (2.24) | 4.16 (3.37) | P < 0.0001 |
| Lubricant Dose/Day | 3.84 (2.42) | 1.59 (2.41) | P < 0.0001 |

Where: MG Expression Score = Meibomian Gland Expression Score.
MG Secretion Score = Meibomian Gland Secretion Score.

Example 4: Effect of a Honey Solution on Subjects with Chronic Sinusitis and Associated Nasolacrimal Obstruction Non-Responsive to Conventional Therapies A clinical trial was performed to evaluate whether a honey solution is a safe and effective treatment in controlling the signs and symptoms of sinusitis and to verify the antimicrobial effects of the honey solution in the nasal cavity.

An aqueous 16.5% w/w honey, 0.9% w/w NaCl and 0.2% w/w benzoic acid solution nasal spray (prepared according to the method of Example 1) was applied intranasally to subjects with a history of chronic sinusitis and associated nasolacrimal obstruction which is non-responsive to conventional therapies (n=27). The honey solution was applied twice daily over a period of one month. Subjective nasal symptoms were evaluated using standardised symptoms surveys, Sino-Nasal Outcome Test-22 (SNOT) Questionnaire v4 and the Lac-Q Lacrimal Symptom Questionnaire. During the study, no adverse effects were reported. 22 subjects (81.5%) reported an improvement in symptoms after treatment with the honey solution.

What is claimed is:

1. A composition comprising honey, a preservative, and an aqueous carrier,
    wherein, by weight of the composition, the honey is present in a therapeutically effective amount in the range of from 2% (w/w) to less than 25% (w/w),
    wherein the preservative is selected from the group consisting of benzoic acid, sorbic acid, a flavonoid, a phenolic acid, abscisic acid, ascorbic acid, pharmaceutically acceptable salts and combinations thereof; and
    wherein the composition is in the form of a nasal lavage, nasal spray, eye drop, eye spray, eye wash, ear wash, ear drop, throat spray, douche, wound dressing hydrator, wound cleansing solution, or lung aspirant.

2. The composition according to claim 1, wherein the honey is present in an amount in the range of from 7 to 18% w/w.

3. The composition according to claim 1, wherein the honey is present in an amount of about 16.5% w/w.

4. The composition according to claim 1, wherein the preservative is benzoic acid or a pharmaceutically acceptable salts thereof.

5. The composition according to claim 4, wherein the salt of benzoic acid is sodium benzoate.

6. The composition according to claim 1, wherein the aqueous carrier is saline.

7. The composition according to claim 1, wherein the honey is substantially sourced from *Leptospermum* species.

8. The composition according to claim 7, wherein the *Leptospermum* species is any one of *Leptospermum scoparium*, *Leptospermum polygalifolium*, *Leptospermum semibaccatum*, *Leptospermum trinervium*, *Leptospermum whitei*, *Leptospermum speciosum*, *Leptospermum liversidgei* and combinations thereof.

9. The composition according to claim 1, wherein the pH of the composition is in the range of from 3.8 to 4.2.

10. The composition according to claim 1, further comprising a rheology modifier.

11. The composition according to claim 10, wherein the rheology modifier is any one of gum arabic, xanthan gum, guar gum, locust bean gum, carboxymethylcellulose, alginate, starch and combinations thereof.

12. The composition according to claim 1, which is in the form of a nasal lavage, eye drop, eye spray, eye wash, ear wash, ear drop, throat spray, douche, wound dressing hydrator, wound cleansing solution or lung aspirant.

13. A method of treatment of a respiratory, ophthalmic, ear or vaginal condition in a subject, comprising administering to the subject a therapeutically effective amount of a composition according to claim 1.

14. The method according to claim 13, wherein the condition is associated with inflammation or infection.

15. The method according to claim 13, wherein the condition is any one of ophthalmic infection, vaginal infection, nasal infection, ear infection, lung infection, sinus infection, throat infection and sore throat.

16. The method according to claim 13, wherein the condition is blepharitis, dry eye syndrome or corneal edema.

17. The method according to claim 13, wherein the condition is rhinitis or sinusitis.

18. A method of hydrating a dressing, comprising contacting the dressing with an effective amount of a composition of claim 1.

19. A method of hydrating or cleaning a wound, comprising contacting the wound with a therapeutically effective amount of a composition of claim 1.

* * * * *

UNITED STATES PATENT AND TRADEMARK OFFICE
CERTIFICATE OF CORRECTION

PATENT NO. : 11,154,578 B2
APPLICATION NO. : 15/327970
DATED : October 26, 2021
INVENTOR(S) : Anthony Peter Moloney It is certified that error appears in the above-identified patent and that said Letters Patent is hereby corrected as shown below:

On the Title Page

In Column 1, Item (73), Line 1, under Assignee, delete "MELGARE" and insert --MELCARE--.

In Column 1, Item (73), Line 2, under Assignee, delete "Mount Cotton (AU)" and insert --Mount Cotton, Queensland (AU)--.

In the Specification

In Column 1, Line 62, delete "baumanii" and insert --baumannii--.

In Column 4, Line 26, delete "bitarate" and insert --bitartrate--.

In Column 5, Line 64, delete "chlorbutanol" and insert --chlorobutanol--.

In Column 6, Line 15, delete "quercitin" and insert --quercetin--.

In Column 7, Lines 8-9 (Approx.), delete "hydroxypropylmethyl cellulose" and insert --hydroxypropylmethylcellulose--.

In Column 7, Lines 55-56, delete "triethylenetetraamine hexaacetic" and insert --triethylenetetramine-hexaacetic--.

In Column 7, Line 63, delete "triethylenetetraamine" and insert --triethylenetetramine--.

In Column 8, Line 33, delete "quinolenes" and insert --quinolones--.

In Column 9, Line 49, delete "25" and insert --25 µm--.

In Column 9, Line 49, delete "10" and insert --10 µm--.

Signed and Sealed this
Twenty-fourth Day of May, 2022

*Katherine Kelly Vidal*
Katherine Kelly Vidal
*Director of the United States Patent and Trademark Office*

In Column 10, Line 12, delete "acanthmoeba" and insert --acanthamoeba--.

In the Claims

In Column 17, Claim 1, Lines 56-57 (Approx.), delete "ascorbic acid, pharmaceutically acceptable salts and combinations thereof;" and insert --ascorbic acid, and pharmaceutically acceptable salts and combinations thereof;--.

In Column 18, Claim 4, Line 12, delete "salts" and insert --salt--.